United States Patent
Aleksov et al.

(10) Patent No.: US 9,967,040 B2
(45) Date of Patent: *May 8, 2018

(54) PATCH SYSTEM FOR IN-SITU THERAPEUTIC TREATMENT

(71) Applicant: Intel Corporation, Santa Clara, CA (US)

(72) Inventors: Aleksandar Aleksov, Chandler, AZ (US); Sasha N. Oster, Chandler, AZ (US); Feras Eid, Chandler, AZ (US); Adel A. Elsherbini, Chandler, AZ (US); Johanna M. Swan, Scottsdale, AZ (US); Amit Sudhir Baxi, Bangalore (IN); Vincent S. Mageshkumar, Navi Mumbai (IN); Kumar Ranganathan, Bangalore (IN); Wen-Ling M. Huang, Los Altos, CA (US)

(73) Assignee: Intel Corporation, Santa Clara, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/676,611

(22) Filed: Aug. 14, 2017

(65) Prior Publication Data

US 2018/0026730 A1  Jan. 25, 2018

Related U.S. Application Data

(63) Continuation of application No. 15/216,502, filed on Jul. 21, 2016, now Pat. No. 9,735,893.

(51) Int. Cl.
*H04B 13/00* (2006.01)
*A61B 5/021* (2006.01)
(Continued)

(52) U.S. Cl.
CPC ......... *H04B 13/005* (2013.01); *A61B 5/0024* (2013.01); *A61B 5/01* (2013.01);
(Continued)

(58) Field of Classification Search
CPC .... H04B 13/005; H04B 5/0012; A61B 5/021; A61B 5/1107; A61B 5/01; A61B 5/1121;
(Continued)

(56) References Cited

U.S. PATENT DOCUMENTS

| | | |
|---|---|---|
| 4,067,342 A | 1/1978 | Burton |
| 4,259,965 A | 4/1981 | Fukuda et al. |

(Continued)

FOREIGN PATENT DOCUMENTS

| | | |
|---|---|---|
| JP | 06333648 A | 12/1994 |
| WO | WO-03065926 A2 | 8/2003 |

(Continued)

OTHER PUBLICATIONS

US 9,865,941, 01/2018, Oster (withdrawn)
(Continued)

*Primary Examiner* — Lewis West
(74) *Attorney, Agent, or Firm* — Schwegman Lundberg & Woessner, P.A.

(57) ABSTRACT

Discussed generally herein are methods and devices including or providing a patch system that can help in diagnosing a medical condition and/or provide therapy to a user. A body-area network can include a plurality of communicatively coupled patches that communicate with an intermediate device. The intermediate device can provide data representative of a biological parameter monitored by the patches to proper personnel, such as for diagnosis and/or response.

20 Claims, 7 Drawing Sheets

(51) Int. Cl.

| | | |
|---|---|---|
| *A61B 5/11* | (2006.01) | |
| *A61B 5/01* | (2006.01) | |
| *A61B 5/00* | (2006.01) | |
| *A61B 5/0402* | (2006.01) | |
| *A61B 5/145* | (2006.01) | |
| *A61N 7/00* | (2006.01) | |
| *A61M 5/142* | (2006.01) | |
| *A61N 1/04* | (2006.01) | |
| *H04B 5/00* | (2006.01) | |

(52) U.S. Cl.
CPC ............ *A61B 5/021* (2013.01); *A61B 5/0402* (2013.01); *A61B 5/1102* (2013.01); *A61B 5/1107* (2013.01); *A61B 5/1121* (2013.01); *A61B 5/14532* (2013.01); *A61B 5/14546* (2013.01); *A61B 5/4839* (2013.01); *A61B 5/4869* (2013.01); *A61B 5/6833* (2013.01); *A61M 5/14248* (2013.01); *A61N 1/0492* (2013.01); *A61N 7/00* (2013.01); *H04B 5/0012* (2013.01)

(58) Field of Classification Search
CPC ... A61B 5/4869; A61B 5/0402; A61B 5/1102; A61B 5/14546; A61B 5/14532; A61B 5/0024; A61B 5/6833; A61B 5/4839; A61N 7/00; A61N 1/0492; A61M 5/14248

See application file for complete search history.

(56) References Cited

U.S. PATENT DOCUMENTS

| | | | |
|---|---|---|---|
| 5,499,927 A | 3/1996 | Ohno et al. | |
| 5,507,303 A | 4/1996 | Kuzma | |
| 6,096,066 A * | 8/2000 | Chen | A61N 5/062 607/88 |
| 6,496,705 B1 * | 12/2002 | Ng | A61B 5/0006 455/456.1 |
| 6,697,262 B2 | 2/2004 | Adams et al. | |
| 7,524,195 B2 | 4/2009 | Ales et al. | |
| 7,637,747 B2 | 12/2009 | Jaatinen et al. | |
| 9,391,394 B2 | 7/2016 | Kockx et al. | |
| 9,735,893 B1 | 8/2017 | Aleksov et al. | |
| 9,893,438 B1 | 2/2018 | Elsherbini et al. | |
| 2006/0124193 A1 | 6/2006 | Orr et al. | |
| 2006/0197213 A1 | 9/2006 | Lian | |
| 2006/0224067 A1 * | 10/2006 | Giftakis | A61N 1/3611 600/483 |
| 2006/0246744 A1 | 11/2006 | Marmaropoulos et al. | |
| 2006/0252284 A1 | 11/2006 | Marmaropoulos et al. | |
| 2007/0100219 A1 | 5/2007 | Sweitzer et al. | |
| 2007/0129776 A1 * | 6/2007 | Robins | A61N 5/0613 607/88 |
| 2008/0004515 A1 * | 1/2008 | Jennewine | A61M 5/14248 600/345 |
| 2009/0054737 A1 * | 2/2009 | Magar | A61B 5/0205 600/300 |
| 2009/0076363 A1 * | 3/2009 | Bly | A61B 5/0205 600/372 |
| 2009/0076559 A1 * | 3/2009 | Libbus | A61N 1/046 607/6 |
| 2009/0131838 A1 * | 5/2009 | Fotiadis | A61B 5/0031 601/2 |
| 2009/0149037 A1 | 6/2009 | Lee et al. | |
| 2009/0182393 A1 * | 7/2009 | Bachinski | A61N 1/325 607/59 |
| 2009/0203244 A1 | 8/2009 | Den Toonder et al. | |
| 2009/0306485 A1 | 12/2009 | Bell et al. | |
| 2010/0125190 A1 | 5/2010 | Fadem | |
| 2010/0136804 A1 | 6/2010 | Strickland | |
| 2010/0304530 A1 | 12/2010 | Yim et al. | |
| 2012/0157807 A1 | 6/2012 | Virtanen et al. | |
| 2012/0238890 A1 | 9/2012 | Baker et al. | |
| 2012/0295451 A1 | 11/2012 | Hyun-jun et al. | |
| 2013/0030259 A1 | 1/2013 | Thomsen et al. | |
| 2013/0065406 A1 | 3/2013 | Rohrbach et al. | |
| 2013/0109937 A1 | 5/2013 | Banet et al. | |
| 2013/0111710 A1 | 5/2013 | Hunts | |
| 2013/0160183 A1 | 6/2013 | Reho et al. | |
| 2013/0166006 A1 * | 6/2013 | Williams | A61N 1/36064 607/116 |
| 2013/0273752 A1 | 10/2013 | Rudisill et al. | |
| 2013/0338746 A1 | 12/2013 | Guvanasen et al. | |
| 2014/0162468 A1 | 6/2014 | Kim | |
| 2014/0335714 A1 | 11/2014 | Schrader | |
| 2015/0087949 A1 | 3/2015 | Felix et al. | |
| 2015/0150502 A1 * | 6/2015 | Wu | A61B 8/0825 604/22 |
| 2015/0303619 A1 | 10/2015 | Kockx et al. | |
| 2016/0045135 A1 | 2/2016 | Kim et al. | |
| 2016/0099517 A1 | 4/2016 | Fernandes et al. | |
| 2016/0121098 A1 | 5/2016 | Kockx et al. | |
| 2016/0157779 A1 | 6/2016 | Baxi et al. | |
| 2016/0172320 A1 | 6/2016 | Swaminathan et al. | |
| 2016/0181729 A1 | 6/2016 | Barth et al. | |
| 2016/0296159 A1 * | 10/2016 | Larson | A61G 7/057 |
| 2018/0020982 A1 | 1/2018 | Elsherbini et al. | |
| 2018/0026393 A1 | 1/2018 | Eid et al. | |

FOREIGN PATENT DOCUMENTS

| | | |
|---|---|---|
| WO | WO-2009036327 A1 | 3/2009 |
| WO | WO-2016010983 A1 | 1/2016 |

OTHER PUBLICATIONS

"U.S. Appl. No. 15/215,531, Non Final Office Action dated May 5, 2017", 13 pgs.

"U.S. Appl. No. 15/215,531, Response filed Jul. 20, 2017 to Non Final Office Action dated May 15, 2017", 17 pgs.

"U.S. Appl. No. 15/216,502, Examiner Interview Summary dated Feb. 1, 2017", 3 pgs.

"U.S. Appl. No. 15/216,502, Non Final Office Action dated Dec. 15, 2016", 15 pgs.

"U.S. Appl. No. 15/216,502, Notice of Allowance dated Apr. 5, 2017", 5 pgs.

"U.S. Appl. No. 15/216,502, Response filed Feb. 17, 2017 to Non Final Office Action dated Dec. 15, 2016", 11 pgs.

"U.S. Appl. No. 15/281,814, Non Final Office Action dated Apr. 10, 2017", 10 pgs "U.S. Appl. No. 15/281,814, Response to Non Final Office Action dated Apr. 10, 2017", 5 pgs.

"International Application Serial No. PCT/US2016/040476, International Search Report dated Jan. 10, 2017", 4 pgs.

"International Application Serial No. PCT/US2016/040476, Written Opinion dated Jan. 10, 2017", 8 pgs "Listen to Your Heart Arrythmias", iRhythm Technologies, [Online]. Retrieved from the Internet: <URL: http://www.irhythmtech.com/patients-heart-arrhythmias-afib.php, (Accessed Mar. 31, 2016), 5 pgs "SEEQ™ Mobile Cardiac Telemetry (MCT) Device", [Online]. Retrieved from the Internet: <URL: http://www.medtronicdiagnostics.com/us/cardiac-monitors/seeq-mct-system/seeq-mct-device/index.htm, (Accessed Mar. 31, 2016), 4 pgs.

Andrew, A. Kostrzewski, et al., "Innovative, wearable snap connector technology for improved networking in electronic garments", (May 2, 2007), 8 pgs.

"U.S. Appl. No. 15/215,531, Final Office Action dated Sep. 22, 2017", 13 pgs.

"U.S. Appl. No. 15/281,814, Notice of Allowance dated Sep. 6, 2017", 7 pgs.

"International Application Serial No. PCT/US2017/037298, International Search Report dated Aug. 14, 2017", 4 pgs.

"International Application Serial No. PCT/US2017/037298, Written Opinion dated Aug. 14, 2017", 7 pgs.

(56) References Cited

OTHER PUBLICATIONS

"International Application Serial No. PCT/US2017/037301, International Search Report dated Sep. 8, 2017", 3 pgs.
"International Application Serial No. PCT/US2017/037301, Written Opinion dated Sep. 8, 2017", 8 pgs.
"International Application Serial No. PCT/US2017/046014, International Search Report dated Nov. 17, 2017", 4 pgs.
"International Application Serial No. PCT/US2017/046014, Written Opinion dated Nov. 17, 2017", 7 pgs.
"International Application Serial No. PCT/US2017/049159, International Search Report dated Dec. 11, 2017", 3 pgs.
"International Application Serial No. PCT/US2017/049159, Written Opinion dated Dec. 11, 2017", 7 pgs.
"U.S. Appl. No. 15/215,531, Notice of Allowability dated Jan. 12, 2018", 2 pgs.
"U.S. Appl. No. 15/215,531, Notice of Allowance dated Dec. 15, 2017", 7 pgs.
"U.S. Appl. No. 15/215,531, Response filed Nov. 14, 2017 to Final Office Action dated Sep. 22, 2017", 12 pgs.
"U.S. Appl. No. 15/267,872, Non Final Office Action dated Nov. 14, 2017", 16 pgs.
"U.S. Appl. No. 15/281,814, Corrected Notice of Allowance dated Jan. 16, 2018", 2 pgs.

\* cited by examiner

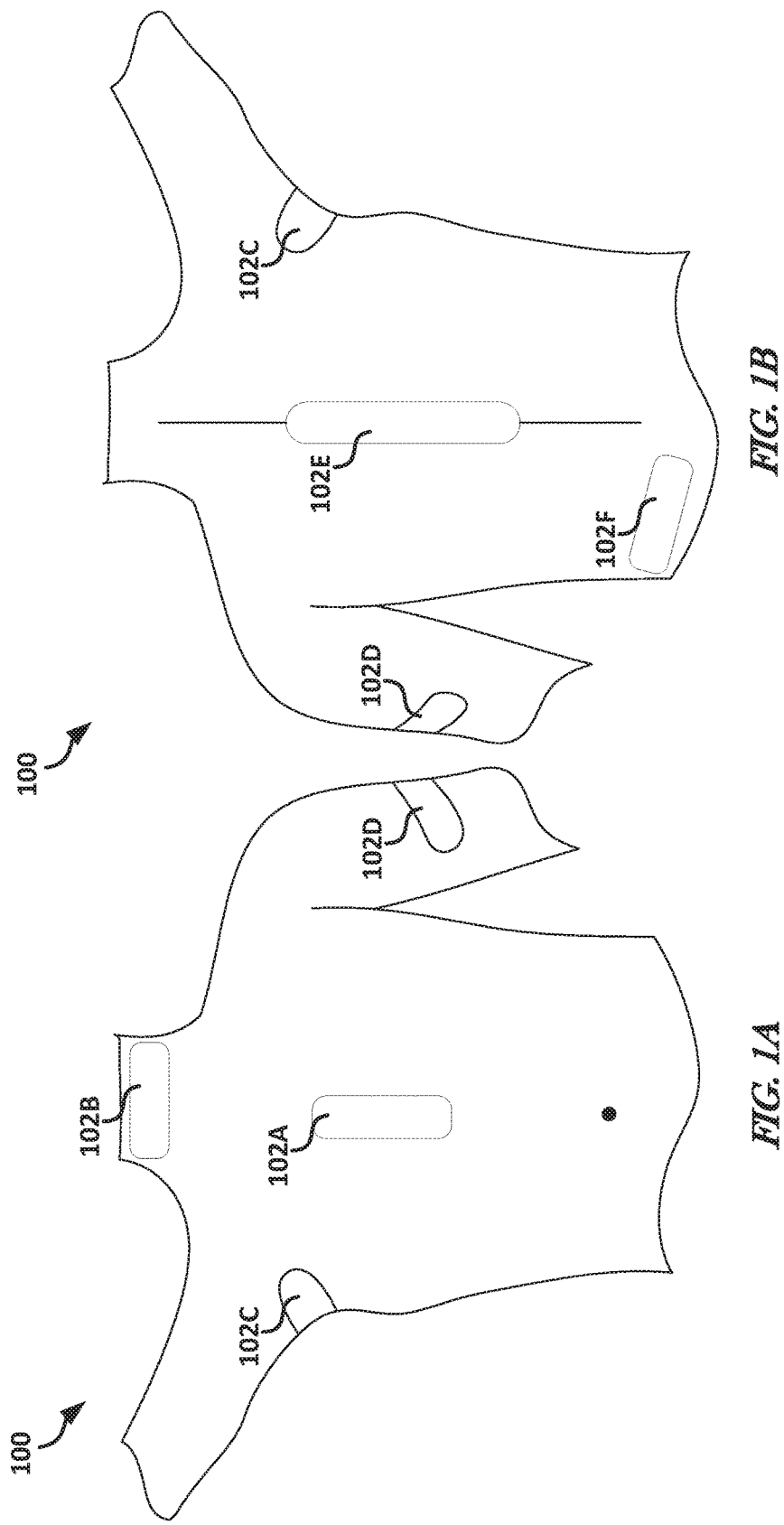

PATCH SYSTEM FOR IN-SITU THERAPEUTIC TREATMENT

CROSS-REFERENCE TO RELATED APPLICATION

This application is a continuation of U.S. patent application Ser. No. 15/216,502, filed Jul. 21, 2016, which is incorporated by reference herein in its entirety.

TECHNICAL FIELD

This disclosure relates generally to providing therapy to a patient using one or more patches. One or more embodiments regard using one or more patches to provide physical, chemical, and/or electrical therapy to a localized region of a patient.

BACKGROUND ART

Biologic indicators can include resistivity, conductivity, absorption, reflectivity, temperature, moisture content, pressure, motion, expansion/contraction, chemical content, or capacitance, among others. Biologic indicators can provide an insight into biologic function. Hospitals often monitor biologic function using dedicated machines, such as a heart rate monitor, a blood pressure monitor, or the like. Such monitors can be cumbersome and generally immobile.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1A illustrates, by way of example, a perspective view diagram of a torso including patches located thereon, in accord with one or more embodiments.

FIG. 1B illustrates, by way of example, another perspective view diagram of a torso including patches located thereon, in accord with one or more embodiments.

DESCRIPTION OF EMBODIMENTS

Figure 2B:
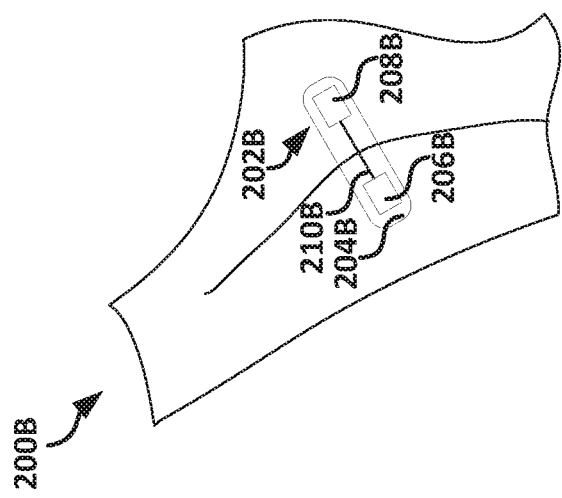
FIG. 2B illustrates, by way of example, another perspective view diagram of another underarm including a patch located thereon, in accord with one or more embodiments.

The following description and the drawings sufficiently illustrate embodiments to enable those skilled in the art to practice them. Other embodiments can incorporate structural, logical, electrical, process, or other changes. Portions and features of some embodiments can be included in, or substituted for, those of other embodiments. Embodiments set forth in the claims encompass all available equivalents of those claims.

One or more embodiments discussed herein can help address a problem of continuous, multi-location, multi sensorial (different biological parameters) data acquisition of biological parameters from the body (such as heart rate, blood pressure, muscle activity, or the like, among others). Multiple inputs can be received from multiple sensors. These multiple inputs can be analyzed, such as to help direct activity (such as exercise/stretch breaks, posture correction, or the like, among others) or suggest intake of prescribed medication (if missed or an adjustment in medication dosage is recommended). Data from the sensors or from performing one or more operations on the data from the sensors (such as by electric and/or electronic processing circuitry) can be provided to one or more health-care providers. The health-care providers can adjust, amend, or revise therapy provided to the patient based on the received data. The change(s) to the therapy can include reprogramming electronics of a patch to adjust how much therapy is provided, when a therapy is provided, what therapy is provided, where the therapy is provided, and/or whether therapy is provided, such as by terminating therapy or adding a therapy.

There are an emerging number of health patches that monitor a singular or a few biological (biophysical/biochemical) parameters at a single location of the body. The most common emerging patches monitor heart-rate and breathing. There is at least one system that monitors transpiration. There are emerging smart-clothes that monitor heart-rate, breathing, and muscle activity.

Embodiments discussed herein can provide one or more advantages over these prior solutions. One or more embodiments can include multiple health patches continuously monitoring a variety of biological parameters. The multiple patches can be communicatively coupled to each other either by means of stretchable interconnects or by wireless means or virtually through an external device. The multiple patches can form a body-area network that can gather and/or provide signals indicative of the bio-information collected by the patch(es). Multiple patches can provide feedback regarding well-defined differentiated locations on the body. One or more of those patches can be used to provide in-situ therapeutic treatment through local heating, ultrasound, chemical (e.g., medicine) dispensing, and/or electric stimulation.

Note that "continuous monitoring" does not necessarily mean every moment in time, but can be sampling (e.g., collecting biometric data for a period of time (e.g., a sub-second, second, minute, hour, etc.) at a specified interval between samples, such as every sub-second, second, minute, hour, day, etc.), depending on the biological parameter being monitored. Continuous monitoring generally occurs over a time period that is orders of magnitude larger than the sampling interval(s).

Current patches for medical (or other) applications are singular systems that are located in one location of the body where some sensory input or therapeutic feedback from the patch may be favored, but other bio information (i.e. inputs to the patch) may be difficult to obtain or impossible to provide feedback for at the location of the patch. Examples are patches on the chest where, for example, a heart rate or ECG signal is well recorded but where the chemical analysis of sweat or monitoring muscle activity in the limbs is hard or not possible. For therapeutic applications, this can significantly limit the available functionality since many disease symptoms involve more than one biological parameter and inaccurately administering a drug can, in some instances, lead to dangerous complications. In one or more embodiments discussed herein, a number of patches can be used to collect a variety of information about the patient condition. This data can help to more accurately diagnose and respond to a symptom.

One or more embodiments include a system of one or more patches. Each patch can produce a signal using one or more sensors. Each signal can be indicative of a biological parameter of the entity wearing the patch. The patches can be placed on a part or area of the body suited for detecting the given biological parameter. The patch can be designed to detect and possibly respond to the signals produced by the one or more sensors, such as by producing an alert, providing the data representative of the signals produced by the one or more sensors to an external device or another patch, performing one or more mathematical operations on the data representative of the signals produced by the one or more sensors (e.g., by encrypting, decrypting, adding, subtracting, multiplying, dividing, compressing, and/or decompressing, or the like).

There are several embodiments of communication in such multi-patch systems. In one embodiment it is "every patch for itself". In such embodiments, the patches collect (and in some embodiments perform operations on) data independently. This data can be provided, independently by each patch, and synthesized into one sensor node, such as a sensor node in the cloud (or a personal mobile/stationary device with sufficient processing power, such as a mobile communications device). In one or more embodiments, each patch can send its respective data to a mobile communication device that may send the data to the sensor node, such as after preprocessing the data, such as by transforming the data to a specified format, encrypting and/or decrypting the data, and/or performing one or more operations on the data. Such an embodiment can be used if a given patch does not possess sufficient computing or battery power to synthesize the sensory information and formulate an adequate therapeutic response by itself or transmit (wirelessly transmit) the data to the sensor node. A program on the phone or in the cloud can then diagnose the condition and prescribe if an action is required (e.g., drug administration, electrical stimulation, physical therapy, exercises, etc.).

In other embodiments, the patches can be communicatively interconnected to each other, such as by communicatively connecting or communicatively coupling one patch directly to one or more other patches. This can be via some stretchable or sufficiently long interconnects that can be independent elements of the system (independent of the patches themselves). Alternatively, the patches can be communicatively coupled to each other via wireless communication between the patches. In one or more embodiments, such patch systems can include a master patch. The master patch can be responsible for at least a portion of data synthesis, in one or more embodiments. The master patch can be responsible for communication with external devices, such as the cloud, mobile communication device, or a stationary computing or communication system. The master device can receive a response from an external computing system (e.g., the cloud, mobile communication device, or stationary mobile or computing device) and transfer it to the patches that are affected by the response (e.g., to those patches that are required to respond).

In one or more other embodiments, there is no dedicated master patch and the patches do not communicate independently with an external device. In some such embodiments, the body-area network in such embodiments can be smart and/or self-organizing. There may be several patches that are able to communicate with external devices and some that are not. In one or more embodiments, only one of the patches can communicate with a device outside the body-area network at once. In such embodiments, which patch will perform that communication task can be determined by the network with respect to the sensory load and available battery power for each patch. This can be achieved by the patches communicating their status to each other and using a heuristic to determine which patch will perform the communication. A body-area network of sensor inputs can be formed using any of the communication protocols discussed.

FIG. 1A illustrates, by way of example, a perspective view diagram of a patch system 100 as viewed from a front-side of a torso. FIG. 1B illustrates, by way of example, a perspective view diagram of the patch system 100 as viewed from a backside of a torso. The patch system 100 as illustrated includes a plurality of adhesive patches 102A, 102B, 102C, 102D, 102E, and 102F. Each of the adhesive patches 102A-F can include one or more substrates with electronics thereon or at least partially therein (see FIG. 6 for an example of a patch 600). Each of the adhesive patches 102A-F can include an adhesive located on a substrate, the adhesive configured to at least temporarily attach the patch 102A-F to skin of an entity to be monitored. Each of the substrates can be stretchable, flexible, stretchable and flexible, or rigid. More details regarding possible embodiments of the patches including details regarding the substrates, electronics, adhesives, among other details, are described in Patent Cooperation Treaty Patent Application PCT/US2016/040476, titled "Devices and Methods for Sensing Biologic Function", and filed on Jun. 30, 2016, which is incorporated herein by reference in its entirety.

The patch 102A is situated on a bust. The patch 102A can include electronics to monitor electrical and/or muscular activity of a heart (e.g., using electrocardiogram (ECG) probes), heart rate, stretch (e.g., using a stretch sensor), organ or conduit (e.g., vein or artery, among others) volume (e.g., using a photoplethysmogram (PPG), such as can include a pulse oximeter), blood or other pressure, temperature (e.g., using a resistance temperature detector), respiration rate (e.g., using a stretch sensor), salinity (e.g., using a salinity sensor), oxygen (e.g., via PPG), a specific force, angular rate, and/or magnetic field (e.g., using an inertial measurement unit (IMU)), breathing rate (e.g., using a stretch sensor), and/or others. A combination of the ECG and PPG can be used to estimate the blood pressure as is described in Patent Cooperation Treaty Application PCT/US2016/040476, referenced supra.

The patch 102B is situated on a neck. The patch 102B can include electronics to monitor muscular and/or electrical activity of the heart (e.g., using an ECG), temperature, stretch, pressure (via piezoelectric materials), organ or conduit (e.g., vein or artery, among others) volume (e.g., using a photoplethysmogram (PPG), such as can include a pulse oximeter), blood pressure (e.g., using a combination of the ECG and PPG), electrical activity, and/or a specific force, angular rate, and/or magnetic field (e.g., using an IMU), among others. This patch can contain EMG monitoring devices that can read out electrical activity of muscles that activate the tongue and larynx and help patients with damaged vocal cords or physiological speech problems communicate with others via speech. This can allow for an increased comfort of the patient, for example after surgery.

The patch 102C is situated, at least partially, in an armpit. The patch 102C can include electronics to monitor temperature, stretch, pressure (via piezoelectric materials), electrical activity, and/or a specific force, angular rate, and/or magnetic field (e.g., using an IMU), and/or salinity, among others.

The patch 102D is situated on an arm. The patch 102D can include electronics to monitor stretch, temperature, electrical activity (e.g., using an EMG), and/or a specific force, angular rate, and/or magnetic field (e.g., using an IMU), among others. A patch on a muscle, as illustrated by the patch 102D in FIG. 1, can monitor electrical and physical activity of the muscle. In addition to alerting the patient or wearer to muscle fatigue due to prolonged or strenuous activity (e.g., through a feedback indicator), such a patch can also include electronics that have devices such as heaters or ultrasound transducers that can help the muscle relax, heal, and/or recover faster form fatigue, thus promoting healing. Some patches over the muscles can include electronics with electrical impulse generators that can periodically trigger the muscle with electrical activity, such as in response to a prolonged period of inactivity being detected. This can improve the quality of stay for many stationary patients and help prevent gangrenes or muscle problems from prolonged periods of immobilization. Such a patch system on a muscle could be used for blood pressure monitoring, such as in conjunction with a patch located on the bust. The patch on the muscle can cross-verify a PPG signal or deliver an additional PPG signal with a greater time delay to the ECG, such as to help improve noise and/or accuracy of the ECG or PPG measurement(s).

The patch 102E is situated along a spine. The patch 102E can include electronics to monitor stretch, temperature, electrical activity, posture (e.g., using one or more stretch sensors or IMUs), and/or a specific force, angular rate, and/or magnetic field, among others.

The patch 102F is situated along a low back, such as over an organ. The organ can be one that has been damaged or is recovering from surgery. Such a patch is shown in FIG. 1. Piezo transducers and/or other sensors of the electronics of the patch can then periodically image the organ or area of the body, such to monitor healing progress.

Figure 3:
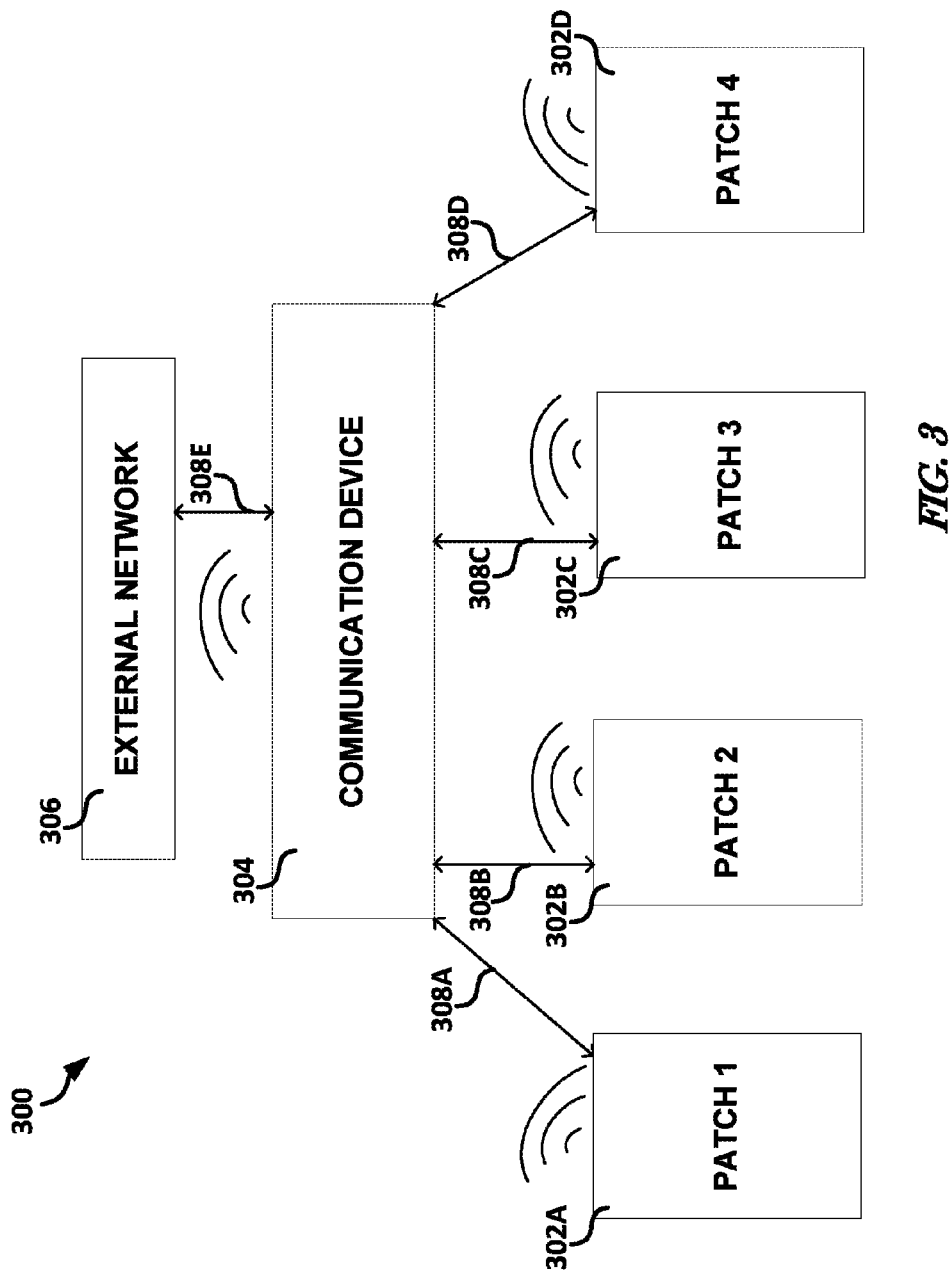
FIG. 3 illustrates, by way of example, a logical block diagram of an embodiment of a patch network.
Figure 4:
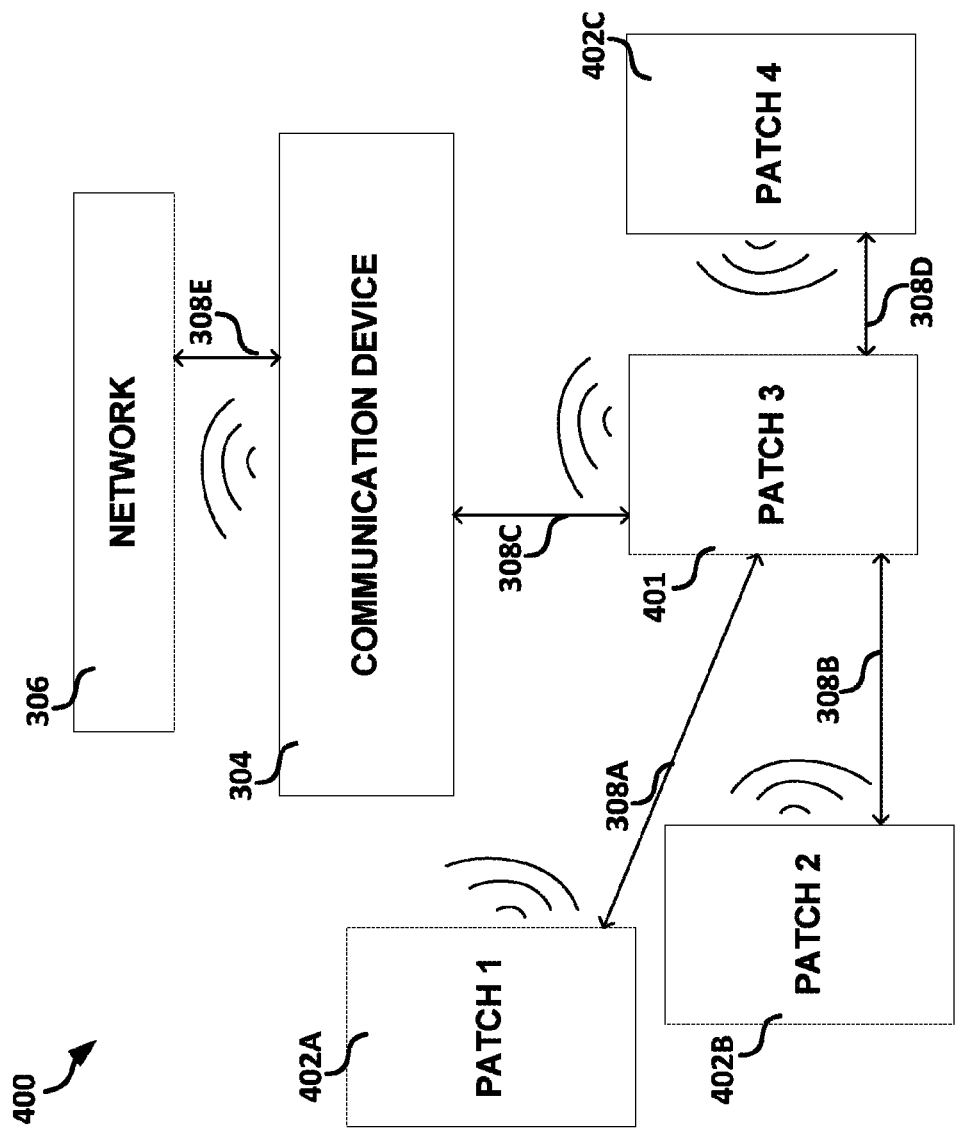
FIG. 4 illustrates, by way of example, a logical block diagram of an embodiment of another patch network.
Figure 5:
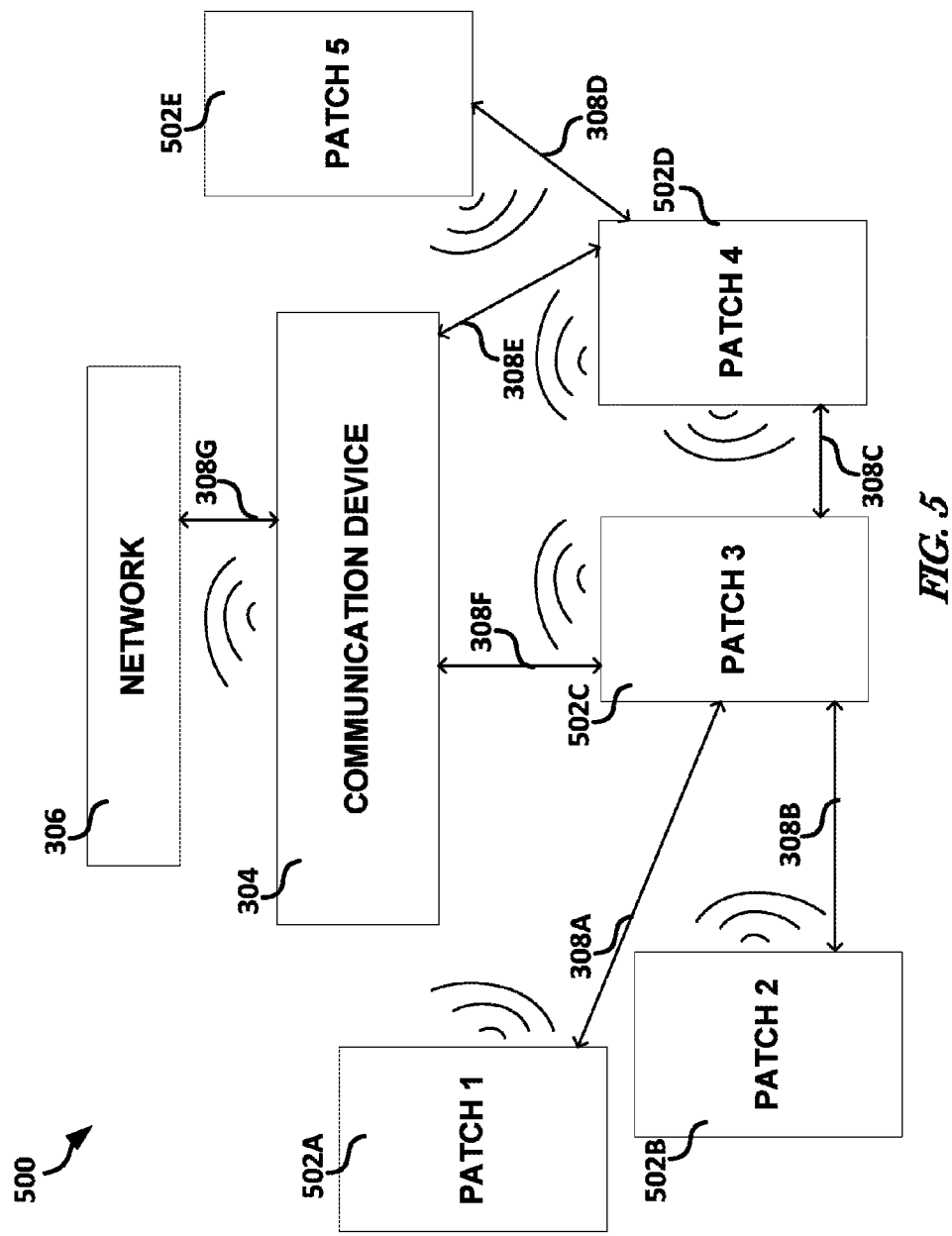
FIG. 5 illustrates, by way of example, a logical block diagram of an embodiment of yet another patch network.

The patches 102A-F can include communication circuitry (e.g., wireless or wired communication circuitry) to communicate information to other patches and/or an external device, such as a mobile device (see FIGS. 3-5). Wired communication circuitry can include physical electrical connections (e.g., conductive wires electrically connected to multiple of the patches or connectors to which an external device can be physically connected to receive data therefrom). Wireless communication circuitry can include one or more radios (e.g., transmit radios, receive radios, and/or transceivers), antennas, modulators, demodulators, amplifiers, or the like to produce or receive a wireless transmission.

The electronics of the patches 102A-F can include electric or electronic components, such as can include a resistor, capacitor, transistor, inductor, diode, regulator, sensor (e.g., a temperature sensor, oxygen sensor, stretch sensor, inertial measurement unit (IMU) sensor, and/or electrocardiogram (ECG) sensor, Electromyography (EMG) sensor, Audio sensor (e.g., microphone could potentially detect heart beat), pressure sensor (e.g., piezo sensor could pick up pulse, heartbeat, fetal movement, etc.), ultrasonic sensor (paired with ultrasound emitter could be used for imaging, heartbeat, fetal features, etc.); chemical sensors such as a salinity or a lactate sensor, optical sensors (to obtain information about levels of certain enzymes/chemicals in blood), among others), accelerometer, optical component (e.g., a light emitting diode (LED)), multiplexer, processor, memory, battery, antenna, modulator/demodulator, radio (e.g., receive or transmit radio or a transceiver), and/or amplifier, or the like. The electronics can be arranged to monitor a biologic parameter of the entity wearing the patch.

In one or more embodiments, the electronics can include: (1) Energy storage (battery or super capacitor) and/or energy harvesting (e.g., solar, RF or temperature based); (2) Data recording functionality (e.g., for skin galvanometer or stretch sensor); (3) Wireless or wired data transfer (for transferring to cell phone or another device) (e.g., Bluetooth, Near field communication (NFC), and/or Cellular, among others); (4) Functional blocks (e.g., one or more IMUs (can be used for data correction or for information on the user)) or temperature sensor (for body temperature sensor) or other types of biosensors (e.g., sensors previously discussed); and/or (5) One or more indicators, such as an LED, or integrated display for real time monitoring of the user's state. Indicators can also be acoustic (e.g., one or more speakers) or haptic feedback (e.g., motors).

Figure 7:
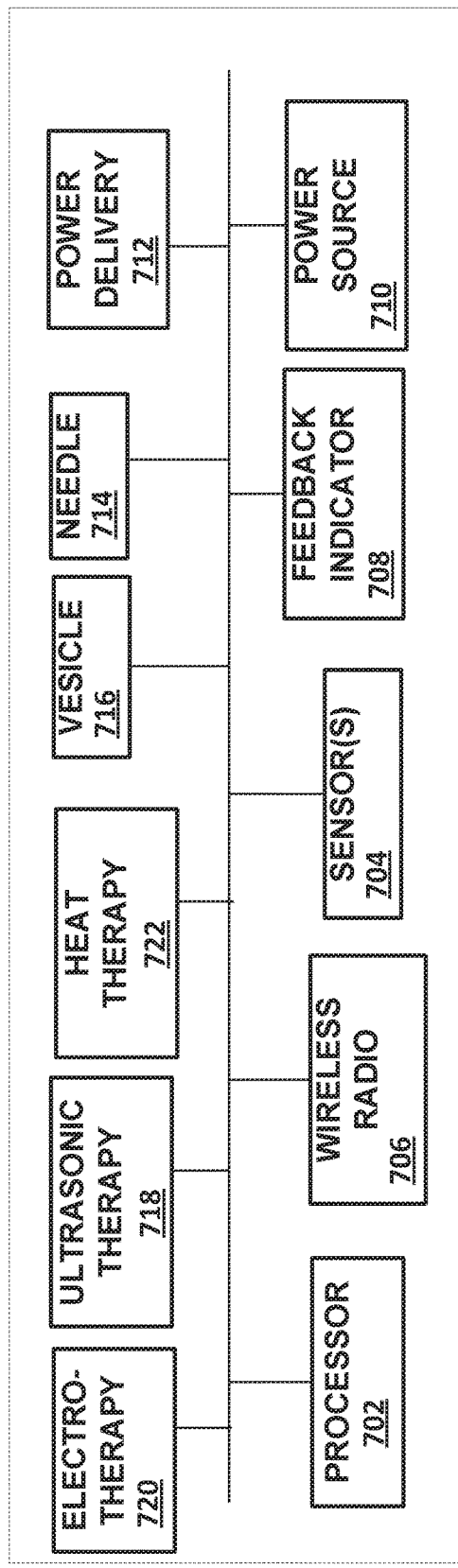
FIG. 7 illustrates, by way of example, a logical circuit diagram of an embodiment of electronics.

The electronics can include a processor, sensor(s), a wireless radio or wired communication circuitry, a feedback indicator, a power source, and power delivery circuitry, among other components. Example components in the electronics are illustrated in FIG. 7.

Figure 2A:
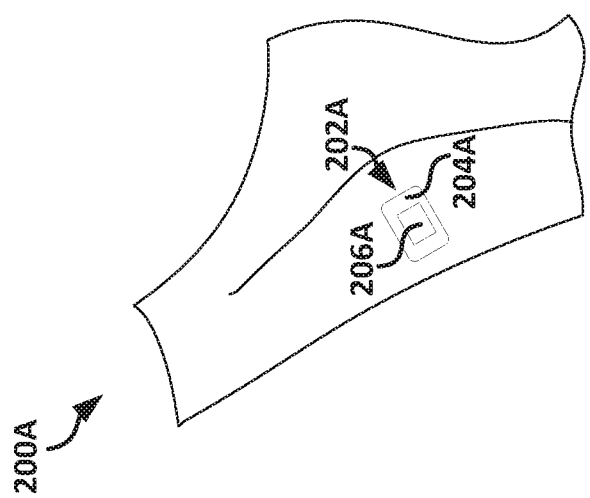
FIG. 2A illustrates, by way of example, a perspective view diagram of an underarm including a patch located thereon, in accord with one or more embodiments.

FIG. 2A illustrates, by way of example, a perspective view diagram of an embodiment of a system 200A that includes a patch 202A situated under an armpit. FIG. 2B illustrates, by way of example, a perspective view diagram of an embodiment of a system 200B that includes another patch 202B situated under the armpit. The patch 202A as illustrated includes a substrate 204A and electronics 206A situated on or at least partially in the substrate 204A. The patch 202B as illustrated includes a substrate 204B with electronics 206B and 208B. The electronics 206B and 208B are electrically connected using a conductive wire 210B. The electronics 206B can be on a flexible circuit board, such as can include a polyimide substrate and the electronics 208B can be on a rigid printed circuit board (PCB). The rigid (e.g., computational) portion of the electronics of the patch 202B can be placed away from under the armpit, such as to increase comfort, such as shown in FIG. 2B.

A patch under the armpit can be used for sensing chemicals in sweat. Chemical data from the sensors under the armpit can be used for an estimation of glucose levels, the presence of certain metabolites, and/or medications, among others. Such data can help in adjusting medication delivery, such as by optimizing and/or reducing the use of medicating agents in the body, such as to help ensure that the medication level is sufficient and no more medication than is needed is getting used. In an example use case of inpatient treatment, these patches can help provide data that helps to control the type and rate of intravenous drugs that are administered. In such embodiments, one or more patches can be electrically connected or coupled to a drug delivery system coupled to the patient.

FIG. 2A illustrates an embodiment in which an entire patch is located under the armpit (this can include the sensor(s), communication/computational electronics, feedback indicator, and/or power source/delivery circuitry). FIG. 2B illustrates an embodiment in which only a portion of the electronics of the patch 202B is under the armpit and another portion of the electronics of the patch are situated on a front or back portion of the body. The sensor(s) can be situated under the armpit and the remaining electric and electronic components can be located on the patch portion outside the armpit and electrically connected to the sensors, such as through meandering or non-meandering traces.

In one or more embodiments, two or more of the patches 102A-F and/or 202A-B can form a body area network. The body area network can provide data for monitoring one or more biological parameters of an entity adorning the body area network. The data from the body area network can be provided to personnel, such as through one or more devices external to the body area network. There are multiple ways in which the data from the patches is provided to the one or more devices external to the network. A few of the ways in which data from the body area network can be provided to one or more devices external to the body area network are provided in FIGS. 3, 4, and 5.

FIG. 3 illustrates, by way of example, a logical block diagram of an embodiment of a system 300 for providing in-situ therapeutic treatment. In the system 300, each patch 302A, 302B, 302C, and 302D communicates signals directly to an intermediate communications device 304, such as a cell phone or tablet. Each patch 302A-D has the ability to communicate with a network 306, such as through the external device 304, but does not have to communicate with other patches 302A-D. In such embodiments, either the network 306 or the external device 304 performs analysis and/or synthesis of data from multiple patches 302A-D. The analysis and/or synthesis can include determining, based on data from two or more patches, whether a medication dosage is too high or too low, whether a therapy (e.g., an ultrasonic or electro-therapy) should be delivered, whether another sensor measurement should be performed by one or more of the patches 302A-D, or the like.

Each of the electronics of the patches 302A-D includes a transceiver and associated circuitry to allow for wireless communication between the external device 304 and the patches 302A-D. The integration of the patches 302A-D into a body area network (and sensor data analysis/synthesis) happens entirely virtual, such as in the network 306 and/or the device 304. In the system 300, each patch 302A-D acts independently of the other patches 302A-D. Electronics of the external device 304 can include a transceiver to receive data from the patches 302A-D and transmit data to the patches 302A-D. The transceiver of the external device can receive data from and transmit data to the network 306. The network 306 can be a network accessible by a nurse, doctor, physician's assistant, or other qualified medical personnel. The data from the communication device 304 to the network 306 can be stored for subsequent analysis by personnel with access to the network 306. The communication device 304, in one or more embodiments, can perform one or more operations on data received. The device 304 can compare the data (before or after the operations) to a specified range of values, such as to determine if an alert is to be sent (by the transceiver) to one or more of the patches 302A-D that includes a feedback indicator and/or to the network 306. In one or more embodiments, the device 304 can provide the alert to the user, such as through a feedback indicator of the electronics of the device 304.

Arrows 308A, 308B, 308C, 308D, and 308E indicate possible directions for data flow using the system 300. While bi-directional communication between each of the patches 308A-D and the device 304 is possible, one or more embodiments may include only uni-directional communication, such as from one or more of the patches 302A-D to the communication device 304 and not vice versa. In such embodiments, electronics of the patch 302A-D may only include a transmit radio (and not a receive radio) and associated circuitry for transmitting data. Consider an embodiment in which a patch is collecting ECG data. This data may be relayed to the device 304 without the device 304 communicating to the patch.

In one or more embodiments, data analysis/synthesis can be performed, at least partially, by electronics of the patch 302A-D. The data before and/or after the synthesis can be communicated to the device 304.

FIG. 4 illustrates, by way of example, a logical block diagram of another embodiment of a system 400 for providing in-situ therapeutic treatment. In the system 400, each patch 402A, 402B, and 402C communicates signals directly to a master patch 401. The master patch 401 is the only patch that communicates with the intermediate communications device 304. Each patch 402A-C has the ability to communicate with the network, such as through the master patch 401 and the external device 304, but does not communicate directly with the device 304. In such embodiments, the network 306, the master patch 401, and/or the external device 304 performs analysis and/or synthesis of data from multiple patches 402A-C.

The master patch 401 can include a battery (or other power source) with a larger capacity than batteries (or other power sources) of the patches 402A-C. The master patch 401 can be configured to receive signals from the patches 402A-C that are time domain multiplexed, frequency domain multiplexed, or other scheme that provides an indication to the master patch 401 which patch 402A-C a given transmission was from. Time domain multiplexing provides the patches 402A-C with different, non-overlapping time slots to communicate with the master patch 401. Frequency domain multiplexing provides the patches 402A-C with different frequency channels over which to communicate with the master patch 401.

In one or more embodiments, the patches 402A-C can provide data to the master patch 401 in response to a memory of the electronics of the respective patch 402A-C including a specified amount of memory stored thereon, a specified amount of time elapsing, determining that data from a sensor of the electronics indicates a biological parameter is in or out of a specified range of values, receiving a communication from the master patch 401 indicating that the patch 402A-C can send the data, or the like.

The master patch 401 is responsible for all communication outside the body area network (i.e. the patches). The master patch 401 can, like the patches 402A-C, monitor, using electronics, one or more biological parameters. The master patch 401 can perform analysis/synthesis of data from the electronics of the master patch 401 and/or one or more of the patches 402A-C.

The master patch 401 is the only patch that communicates with the intermediate communications device 304. Each patch 402A-C has the ability to communicate with the network, such as through the master patch 401 and the external device 304, but does not communicate directly with the device 304. In such embodiments, the network 306, the master patch 401, and/or the external device 304 performs analysis and/or synthesis of data from multiple patches 302A-C.

FIG. 5 illustrates, by way of example, a logical block diagram of another embodiment of a system 500 for providing in-situ therapeutic treatment. In the system 500, each patch 502A, 502B, 502C, 502D, and 502E can take a role of a master patch or a slave patch. One patch 502C can take the role of the master patch at a first time and another patch 502D can take the role of the master patch at a different time. The master patch 502C-D at a given time is the only patch that communicates to the device 304. The slave patches (any patch 502A-E that is not the master patch at a given time) communicate to the master patch and not with the device 304.

In one or more embodiments, a patch performs a role of a hybrid master-slave. A hybrid master-slave receives data from another patch and forwards the data to a master patch, but does not communicate directly with the device 304 when the hybrid master-slave is not performing a master role. For example, when the patch 502C is performing the role of the master, the patch 502E can provide data to the patch 502D and the patch 502D can provide the data from both patches 502D and 502E to the patch 502C. The patch 502C can then communicate data from all the patches 502A-E to the device 304, such as simultaneously (in a same packet) or in a time multiplexed or frequency multiplexed manner.

The patch that acts as a master can be determined based on a heuristic or a pre-defined schedule. The heuristic can be based on available power at the patch, power usage of the patch, proximity to the device 304, and/or range of a wireless radio of the patch, among others. Data indicating which patch is determined to be a master can be communicated, such as by a current master patch, to remaining patches. The patch can then act as master, such as for a certain period of time, and the heuristic can be re-computed for each of the patches. The current master can then remain the master or a new master can be declared and the new master can act as a master, such as for a specified period of time. Such embodiments can provide for a more even power-use distribution among the power sources of the patches. There can be slave patches that remain slaves as they have no capability to radio to outside of the body network, but to limit power, for example, all communication these patches are capable of is within the body-area network. Thus, FIG. 5 illustrates a block diagram of a body-area multi-patch network with dynamic and autonomous patch assignments. Slave patches are patches that do not communicate to the outside world either due to assignment or if they were designed only to work within a body-area network. A master patch is the patch (or the patches) responsible for communication with the outside (of the body-area) network.

Communication between patches is an analogue to communication between any two or more computational devices. Sensor fusion and data transfer to and from the cloud is also a reality. Wireless radios for low power exist and components of the above mentioned sensors and electronics exist. These concepts and items are used in a system, as it would be any wireless networked system, however this one based on flexible and stretchable systems on the human body to provide functionality to monitor biological parameters of an entity wherein the patches. Such body area networks provide an ability to provide unique functionality and/or provide one or more advantages over current systems and methods for monitoring such biological parameters.

The data of the body-area multi-patch system (i.e. the data collected and/or processed by the patches of the body-area system) can be analyzed by a computing system capable of sensor-fusion, machine learning, and/or connected to a database of physiological signals and responses to correctly analyze the state of the patient and formulate a response. All these systems can include components including CPU's, co-processors, and/or wireless radios, among other electronics.

In one or more embodiments, one or more of the patches can communicate directly with one or more other patches of the body-area network, such as for better response to biological parameters. For example, an increase of perspiration not related to increased muscle activity or heart rate can be an alarming sign that can be detected when the sensors of the multi patch system work together to allow for the synthesis of an overall body view that cannot be captured by a single patch. In another example, if an increase in heart rate (e.g., not tachycardia or other arrhythmia) is not associated with increased muscular activity, motion, or breathing this can also be a sign for concern. Fluctuations in blood pressure not associated with changes in heart rate can be associated with problems of the circulatory system other than the heart. An increase in pain related chemicals in the sweat can be checked against the posture of the patient either indicating bad posture leading to pain or the pain leading to bad posture to counteract it (depending on the patient situation). This combined sensory input can then lead to a more comprehensive and corrective therapeutic input of personnel (e.g., medical professional) monitoring the patient.

Figure 6:
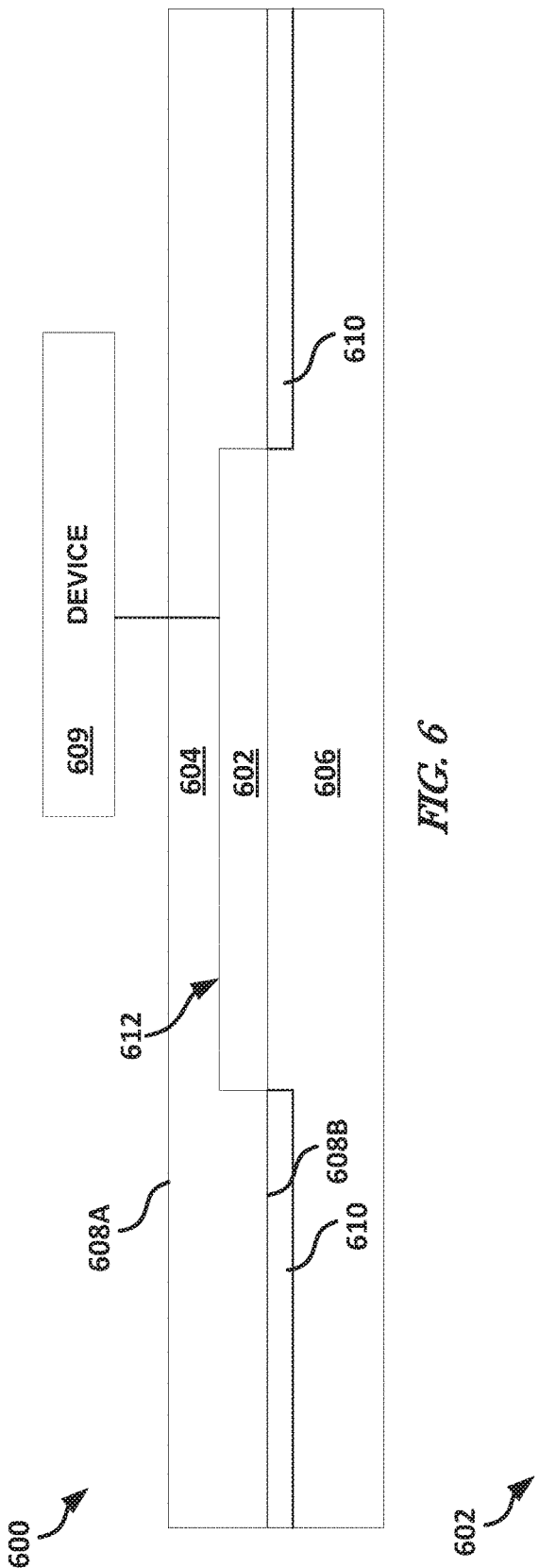
FIG. 6 illustrates, by way of example, a cross-section diagram of an embodiment of a patch.

FIG. 6 illustrates, by way of example, a logical block diagram an embodiment of a patch 600. The patch 600 as illustrated includes electronics 602 and a substrate 604. The electronics 602 can be arranged to monitor a biologic parameter of the entity wearing the patch and/or to provide therapy to the entity wearing the patch 600.

The substrate 604 can include a stretchable and/or flexible material, such as can include an elastomer, spandex, woven fabric, plastic (e.g., polyvinyl chloride (PVC), polyethylene, and/or polyurethane), TPU (thermoplastic polyethylene), polydimethylsiloxane (PDMS) (silicone), latex, or a combination thereof, among others. As used herein "stretchable" and "flexible" are different. Stretchable connotes an ability to lengthen and flexible connotes an ability to rotate.

The electronics 602 can be on a top surface 608A of the substrate 604. An adhesive 610 on a bottom surface 608B of the substrate 604. The bottom surface 608B is opposite the top surface 608A. The bottom surface 608B faces skin 606 of a user. The top surface 608A faces away from the skin 606 of the user. The substrate 604 can be optically transparent, such as to allow light from the electronics 602 to be incident on the skin 606.

The electronics 602 can be electrically coupled to a device 609. The device can include an insulin pump or other device that does not fit (e.g., comfortably) on the patch 600. In an embodiment in which the device 609 includes an insulin pump, the electronics 602 can include circuitry to control release of insulin from the pump. In such embodiments, the electronics 602 of that same patch or another patch can include circuitry to monitor blood sugar level. The blood sugar level information can be provided to the circuitry that controls the release of the insulin, such as to help regulate the blood sugar level of the user.

The adhesive 610 can at least temporarily affix the patch 600 to the skin 606. The adhesive 610 can include a double-sided tape or an acrylate (e.g., methacrylate or epoxy diacrylate, among others), among others.

A cavity 612 can be formed in the substrate 604. The electronics 602 can be situated, at least partially, in the cavity 612. The adhesive 610, as illustrated, is located on portions of the substrate 604 around the electronics 602. In one or more embodiments, the adhesive 610 can be located on the electronics 602.

FIG. 7 illustrates, by way of example, a logical circuit diagram of an embodiment of the electronics 602. The electronics 602 as illustrated include a processor 702, sensor(s) 704, wireless radio 706, feedback indicator 708, power source 710, power delivery circuitry 712, needle 714, vesicle 716, ultrasonic therapy circuitry 718, electro-therapy circuitry 720, and heat therapy circuitry 722.

The processor 702 includes electric or electronic components arranged to perform operations on signals received at the processor. The processor 702 can include an application specific integrated circuit (ASIC), field programmable gate array (FPGA), or the like. The processor 702 can receive signals from the sensor(s) 704, the wireless radio 706, and the power delivery circuitry 712. The processor 702 can include an analog to digital converter (ADC). The power delivery circuitry 712 can provide the processor 702 with the electrical power required for the operation of the processor 702.

The sensor(s) 704 can include one or more of an ECG electrode, electro-dermal activity sensor, a stretch sensor, a photo diode (or other light detector), a temperature detector, a salinity sensor, a power level sensor, a pulse oximeter, a blood-glucose sensor, and/or a resistivity sensor, among others, such as can include one or more sensors discussed herein. One or more of the sensor(s) 704 may require electrical power to operate, such power can be provided directly from the power source 710 or from the power delivery circuitry 712.

The wireless radio 706 can include a receiver, transmitter, transceiver, antenna, modulator, demodulator, amplifier, and/or other circuitry associated with receiving and/or transmitting electrical signals in a wireless manner. The wireless radio 706 can provide signals received to the processor. The wireless radio 706 can transmit signals received from the processor 702. The wireless radio 706 can be powered directly by the power source or the power delivery circuitry 712.

The feedback indicator 708 can include an audio, visual, and/or tactile feedback component. An audio feedback component can include a speaker and associated signal conditioning circuitry, such as an amplifier. A visual feedback component can include a display, such as a touch screen display, LED display, liquid crystal display (LCD), or the like. A tactile feedback component can include a motor, a fan, a heat generating component, or the like.

The power source 710 can include a dry cell battery, a super capacitor, a solar panel, an inductive coupler, or the like. The power source 710 can provide electrical power directly to any of the processor 702, the sensor(s) 704, the wireless radio 706, the feedback indicator 708, the ultrasonic therapy circuitry 718, electro-therapy circuitry 720, heat therapy circuitry 722, and/or the power delivery circuitry 712. In one or more embodiments, one or more patches can be powered by energy harvesting, one or more patches can be powered by battery power, and/or one or more patches can be powered by a combination of both.

The power delivery circuitry 712 can receive power from the power source 310 and modify one or more of the current and voltage of the power to be compliant with a power requirement of a component to receive the power. The power delivery circuitry 712 can include one or more of a voltage regulator, current regulator, current source, voltage booster, current booster, amplifier, or the like to alter a current or voltage of the electrical power from the power source 710.

The processor 702 can receive signals from the sensor(s) and perform operations based on the state of the signals received. For example, the processor 702 can receive a signal from one of the sensor(s) and compare a value corresponding to the signal, to one or more threshold values. If the value is less than (or equal to), greater than (or equal to), or a combination thereof, one or more of the threshold values, the processor 702 can perform an operation in response thereto. The operation can include providing a signal to the feedback indicator 708 that causes the feedback indicator 708 to indicate that the monitored value is in or out of range. In another example, the processor 702 can perform operations on signals received from one or more of the sensor(s) to determine a value associated with a biologic parameter. For example, the processor 702 can receive signals from an ECG electrode and a photo detector and determine an estimate of blood pressure based on those signals. In another example, the processor 702 can receive signals from a stretch sensor and determine a respiration rate based on those receive signals.

In one or more embodiments, one or more of the patches can include components that penetrate the skin for direct blood chemistry monitoring or direct administration of medicine into the body (does not have to be absorbed by the skin first). The needle 714 can include a pointed hollow tube that can deliver a chemical agent under the surface of the skin of the user. The needle 714 can be mechanically coupled to the vesicle 716. The vesicle 716 is a container for medication, or other chemical agent, that can be provided to a surface of the skin or under the surface of the skin (e.g., through the needle). The one or more vesicles 716 that can be opened, such as in response to determining that one or more biological parameters are in a specified range of values (such as by one or more of the patches, the mobile communications device, or the network). The one or more vesicles 716 can release the chemical agent onto the skin, such that the skin can absorb at least some of the chemical agent, such as for drug delivery. Such embodiments can include a vesicle 716 and not include a needle.

The ultrasonic therapy circuitry 718 includes an ultrasonic transducer that converts electrical energy to an ultrasonic wave. The ultrasonic therapy circuitry 718 can produce data of an ultrasound image of the body or can provide ultrasonic waves as therapy (e.g., with no imaging or data gathering).

The electro-therapy circuitry 720 includes one or more conductive pads. The conductive pads can provide electrical stimulation to the area around the conductive pads. Electrical stimulation can help increase blood flow and/or relax a muscle.

The heat therapy circuitry 722 can include a heat transducer that coverts electrical energy to heat energy. The heat therapy circuitry 722 can include a heater coil, a conductive material, or other heating element.

Manufacturing, structure, materials, function, and other patch details are discussed in other applications, such as Patent Cooperation Treat Application PCT/US2016/040476, referenced herein.

Figure 8:
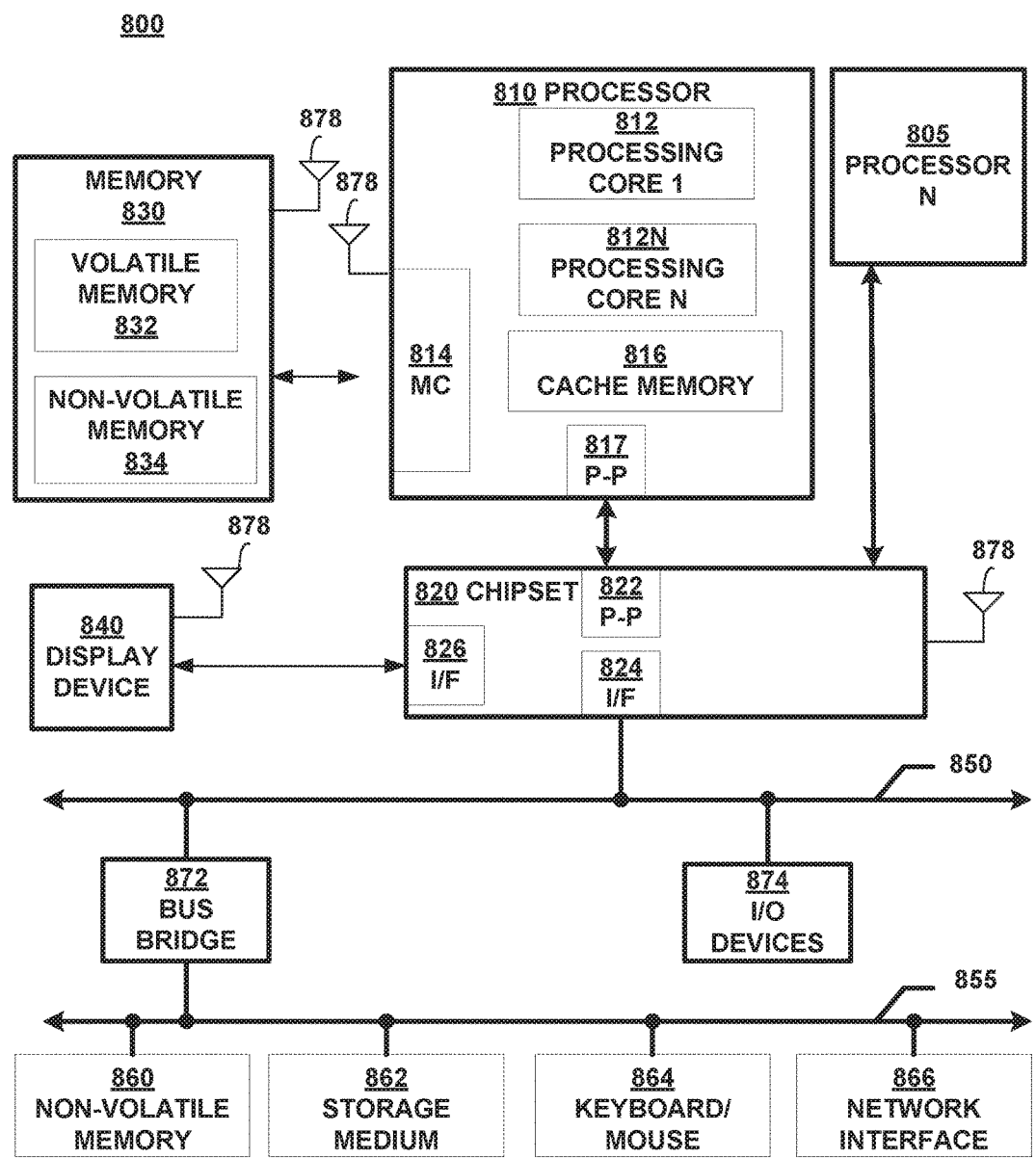
FIG. 8 illustrates, by way of example, a logical block diagram example of an electronic device which includes items that can be used in a device of the network of FIG. 3, FIG. 4, or FIG. 5 or in a patch of FIGS. 1A-1B, 2A-2B, or 6, such as in the electronics.

FIG. 8 illustrates, by way of example, a logical block diagram of an embodiment of system 800. In one or more embodiments, system 800 includes one or more components that can be included in or connected to the electronics 602 in one or more embodiments.

In one embodiment, processor 810 has one or more processing cores 812 and 812N, where 812N represents the Nth processor core inside processor 810 where N is a positive integer. In one embodiment, system 800 includes multiple processors including 810 and 805, where processor 805 has logic similar or identical to the logic of processor 810. In some embodiments, processing core 812 includes, but is not limited to, pre-fetch logic to fetch instructions, decode logic to decode the instructions, execution logic to execute instructions and the like. In some embodiments, processor 810 has a cache memory 816 to cache instructions and/or data for system 800. Cache memory 816 may be organized into a hierarchal structure including one or more levels of cache memory.

In some embodiments, processor 810 includes a memory controller 814, which is operable to perform functions that enable the processor 810 to access and communicate with memory 830 that includes a volatile memory 832 and/or a non-volatile memory 834. In some embodiments, processor 810 is coupled with memory 830 and chipset 820. Processor 810 may also be coupled to a wireless antenna 878 to communicate with any device configured to transmit and/or receive wireless signals. In one embodiment, the wireless antenna interface 878 operates in accordance with, but is not limited to, the IEEE 802.11 standard and its related family, Home Plug AV (HPAV), Ultra Wide Band (UWB), Bluetooth, WiMax, or any form of wireless communication protocol.

In some embodiments, volatile memory 832 includes, but is not limited to, Synchronous Dynamic Random Access Memory (SDRAM), Dynamic Random Access Memory (DRAM), RAMBUS Dynamic Random Access Memory (RDRAM), and/or any other type of random access memory device. Non-volatile memory 834 includes, but is not limited to, flash memory, phase change memory (PCM), read-only memory (ROM), electrically erasable programmable read-only memory (EEPROM), or any other type of non-volatile memory device.

Memory 830 stores information and instructions to be executed by processor 810. In one embodiment, memory 830 may also store temporary variables or other intermediate information while processor 810 is executing instructions. In the illustrated embodiment, chipset 820 connects with processor 810 via Point-to-Point (PtP or P-P) interfaces 817 and 822. Chipset 820 enables processor 810 to connect to other elements in system 800. In some embodiments of the invention, interfaces 817 and 822 operate in accordance with a PtP communication protocol such as the Intel® QuickPath Interconnect (QPI) or the like. In other embodiments, a different interconnect may be used.

In some embodiments, chipset 820 is operable to communicate with processor 810, 805N, display device 840, and other devices. Chipset 820 may also be coupled to a wireless antenna 878 to communicate with any device configured to transmit and/or receive wireless signals.

Chipset 820 connects to display device 840 via interface 826. Display 840 may be, for example, a liquid crystal display (LCD), a plasma display, cathode ray tube (CRT) display, or any other form of visual display device. In some embodiments of the invention, processor 810 and chipset 820 are merged into a single SOC. In addition, chipset 820 connects to one or more buses 850 and 855 that interconnect various elements 874, 860, 862, 864, and 866. Buses 850 and 855 may be interconnected together via a bus bridge 872. In one embodiment, chipset 820 couples with a non-volatile memory 860, a mass storage device(s) 862, a keyboard/mouse 864, and a network interface 866 via interface 824 and/or 804, etc.

In one embodiment, mass storage device 862 includes, but is not limited to, a solid state drive, a hard disk drive, a universal serial bus flash memory drive, or any other form of computer data storage medium. In one embodiment, network interface 866 is implemented by any type of well-known network interface standard including, but not limited to, an Ethernet interface, a universal serial bus (USB) interface, a Peripheral Component Interconnect (PCI) Express interface, a wireless interface and/or any other suitable type of interface. In one embodiment, the wireless interface operates in accordance with, but is not limited to, the IEEE 802.11 standard and its related family, Home Plug AV (HPAV), Ultra Wide Band (UWB), Bluetooth, WiMax, or any form of wireless communication protocol.

While the components shown in FIG. 8 are depicted as separate blocks within the system 800, the functions performed by some of these blocks may be integrated within a single semiconductor circuit or may be implemented using two or more separate integrated circuits. For example, although cache memory 816 is depicted as a separate block within processor 810, cache memory 816 (or selected aspects of 816) can be incorporated into processor core 812.

Additional Notes and Examples

In Example 1 a system can include a first patch including a first flexible, stretchable substrate, a first adhesive on the first flexible, stretchable substrate, the first adhesive configured to temporarily attach the first patch to skin of a user, and first electronics on or at least partially in the first flexible, stretchable substrate, the first electronics including at least one first component to provide therapy to the user and a first wireless radio, and a second patch including a second flexible, stretchable substrate, a second adhesive on the second flexible, stretchable substrate, the second adhesive configured to temporarily attach the second patch to the skin of the user, and second electronics on or at least partially in the second flexible, stretchable substrate, the second electronics including at least one second component to monitor a first biological parameter of the user; and a wireless communication device communicatively coupled to the first wireless radio of the first electronics, the wireless communication device including processing circuitry to receive data corresponding to the first biological parameter and provide one or more signals to the first patch to adjust an amount of the therapy provided by the first patch.

In Example 2, Example 1 can further include, wherein the at least one first component includes at least one of a vesicle and a needle and the therapy includes medicine, the at least one first component includes an ultrasonic transducer and the therapy include ultrasonic waves, and the at least one first component includes one or more conductive pads coupled to power delivery circuitry and the therapy includes electrical stimulation.

In Example 3, at least one of Examples 1-2 can further include, wherein the wireless communication device is further communicatively coupled to a second wireless radio of the second electronics to receive the data corresponding to the first biological parameter.

In Example 4, at least one of Examples 1-3 can further include, wherein the first patch operates in a master role including the first wireless radio communicatively coupled to the second wireless radio and the second wireless radio is not communicatively coupled to the wireless communication device.

In Example 5, at least one of Examples 1-4 can further include, a third patch including a third flexible, stretchable substrate, a third adhesive on the third flexible, stretchable substrate, the third adhesive configured to temporarily attach the third patch to the skin of the user, and third electronics on or at least partially in the third flexible, stretchable substrate, the third electronics including at least one third component to monitor a second biological parameter of the user and a third wireless radio, the second biological parameter different from the first biological parameter, the third wireless radio communicatively coupled to at least one of the first wireless radio, the second wireless radio, and the wireless communication device.

In Example 6, Example 5 can further include, wherein the third wireless radio is communicatively coupled to the second wireless radio and the second wireless radio is communicatively coupled to the first wireless radio and the second and third wireless radios are not communicatively coupled to the wireless communication device.

In Example 7, at least one of Examples 1-6 can further include, wherein the first biological parameter includes one of flexion, contraction, stretch, temperature, electrical activity a specific force, angular rate, magnetic field, salinity, muscular activity of the heart, electrical activity of the heart, pulse, oxygen content, lactate content, pressure, organ or conduit volume, blood pressure, blood glucose level, and electro-dermal activity.

In Example 8, at least one of Examples 1-7 can further include, wherein the second patch is configured to be situated partially in an armpit with a first portion of the electronics on a first electronics substrate configured to be situated in the armpit and a second portion of the electronics on a second electronics substrate electrically coupled to the first portion of the electronics and configured to be situated outside of the armpit.

In Example 9, Example 8 can further include, wherein the first electronics substrate is flexible and the second electronics substrate is rigid.

In Example 10, at least one of Examples 1-9 can further include, wherein the second wireless radio and the first wireless radio are configured to communicate directly with the wireless communication device.

Example 11 can include a method comprising attaching, using a first adhesive on a first flexible, stretchable substrate, a first patch to skin of a user at a first location, attaching, using a second adhesive on a second flexible, stretchable substrate, a second patch to the skin of the user at a second, different location, monitoring, using second electronics on or at least partially in the second flexible, stretchable substrate, a first biological parameter of the user during a first time frame, providing, using one of a first wireless radio of the first electronics and a second wireless of the second electronics, signals corresponding to the first biological parameter to a wireless communication device, and providing, using the first electronics on or at least partially in the first substrate and during the first time frame, a therapy to the user.

In Example 12, Example 11 can include, wherein a first component of the first electronics includes an ultrasonic transducer and the therapy includes ultrasonic therapy.

In Example 13, at least one of Examples 11-12 can further include, wherein a first component of the first electronics includes at least one conductive pad and the therapy includes electro-therapy provided through the at least one conductive pad.

In Example 14, at least one of Examples 11-13 can further include, wherein a first component of the first electronics includes at least one of a vesicle and a needle and the therapy includes a medication provided through the at least one vesicle and the at least one needle.

In Example 15, at least one of Examples 11-14 can further include, attaching, using a third adhesive on a third flexible, stretchable substrate, a third patch to skin of a user at a third location, monitoring, using third electronics on or at least partially in the third flexible, stretchable substrate, a second biological parameter of the user during the first time frame, and providing, using one of the first wireless radio of the first electronics and the second wireless radio of the second electronics, signals corresponding to the second biological parameter to the wireless communication device.

In Example 16, at least one of Examples 11-15 can further include receiving, from the wireless communication device and at one of the first wireless radio of the first electronics and the second wireless radio of the second electronics, signals indicating a change to the therapy provided by the first electronics, the change to the therapy determined based on the signals corresponding to the first biological parameter, and adjusting an amount or a schedule of therapy delivery based on the signals from the wireless communication device.

Example 17 can include a system comprising a body area network comprising at least two patches, each of the at least two patches including a flexible, stretchable substrate, an adhesive on the flexible, stretchable substrate, the adhesive configured to temporarily attach the patch to skin of a user, and electronics on or at least partially in the flexible, stretchable substrate, the electronics including a wireless radio and at least one of a first component to provide therapy to the user and a second component to monitor a first biological parameter of the user, and a wireless communication device communicatively coupled to at least one patch of the at least two patches of the body area network, the wireless communication device including processing circuitry to receive data corresponding to the biological parameter and provide one or more signals to a first patch of the at least two patches to adjust an amount of the therapy provided by the first patch.

In Example 18, Example 17 can further include, wherein each patch of the at least two patches is communicatively coupled to the wireless communication device to communicate directly with the wireless communication device.

In Example 19, at least one of Examples 17-18 can further include, wherein only one patch of the at least two patches is communicatively coupled to the wireless communication device to communicate data from all patches of the at least two patches to the wireless communication device.

In Example 20, at least one of Examples 17-19 can further include, wherein a first patch of the at least two patches is configured to perform a role of a master patch during a first time frame and all other patches of the at least two patches provide data to the first patch during the first time frame and a second patch of the at least two patches is configured to perform the role of the master patch during a second time frame different from the first time frame and all other patches of the at least two patches provide data to the second patch during the second time frame.

The above description of embodiments includes references to the accompanying drawings, which form a part of the description of embodiments. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above description of embodiments, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the description of embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system comprising:
a first patch including:
a first flexible and/or stretchable substrate, a first adhesive on the first substrate, the first adhesive configured to temporarily attach the first patch to skin of a user, and first electronics on or at least partially in the first substrate, the first electronics including at least one first component to provide therapy to the user and a first wireless radio, and a second patch including:
a second flexible and/or stretchable substrate, a second adhesive on the second substrate, the second adhesive configured to temporarily attach the second patch to the skin of the user, and second electronics on or at least partially in the second flexible, stretchable substrate, the second electronics including at least one second component to monitor a first biological parameter of the user and a second wireless radio; and
the second wireless radio communicatively coupled to the first wireless radio of the first electronics, the second wireless radio to provide one or more signals indicative of the first biological parameter to the first patch.

2. The system of claim 1, wherein the first electronics are to adjust an amount of the therapy provided by the first patch in response to the provided one or more signals.

3. The system of claim 1, wherein the at least one first component includes at least one of a vesicle and a needle and the therapy includes medicine, the at least one first component includes an ultrasonic transducer and the therapy include ultrasonic waves, and the at least one first component includes one or more conductive pads coupled to power delivery circuitry and the therapy includes electrical stimulation.

4. The system of claim 3, wherein the first patch operates in a master role including the first wireless radio communicatively coupled to the second wireless radio and the second wireless radio communicates to another device through the first patch.

5. The system of claim 1, further comprising:
a third patch including:
a third flexible and/or stretchable substrate, a third adhesive on the third substrate, the third adhesive configured to temporarily attach the third patch to the skin of the user, and third electronics on or at least partially in the third substrate, the third electronics including at least one third component to monitor a second biological parameter of the user and a third wireless radio, the second biological parameter different from the first biological parameter, the third wireless radio communicatively coupled to at least one of the first wireless radio and the second wireless radio.

6. The system of claim 5, wherein the third wireless radio is communicatively coupled to the second wireless radio and the second wireless radio is communicatively coupled to the first wireless radio and the second and third wireless radios are not communicatively coupled to another device to which the first wireless radio is communicatively coupled.

7. The system of claim 1, wherein the first biological parameter includes one of flexion, contraction, stretch, temperature, electrical activity a specific force, angular rate, magnetic field, salinity, muscular activity of the heart, electrical activity of the heart, pulse, oxygen content, lactate content, pressure, organ or conduit volume, blood pressure, blood glucose level, and electro-dermal activity.

8. The system of claim 1, wherein the second patch is configured to be situated partially in an armpit with a first portion of the electronics on a first electronics substrate configured to be situated in the armpit and a second portion of the electronics on a second electronics substrate electrically coupled to the first portion of the electronics and configured to be situated outside of the armpit.

9. The system of claim 8, wherein the first electronics substrate is flexible and the second electronics substrate is rigid.

10. The system of claim 1, wherein the second wireless radio and the first wireless radio are both further configured to communicate directly with another device.

11. A method comprising:
attaching, using a first adhesive on a first flexible and/or stretchable substrate of a first patch, the first patch to skin of a user at a first location;
attaching, using a second adhesive on a second flexible and/or stretchable substrate of a second patch, the second patch to the skin of the user at a second, different location;
monitoring, using second electronics on or at least partially in the second substrate, a first biological parameter of the user during a first time frame;
providing, using a second wireless radio of the second electronics, signals corresponding to the first biological parameter to a first wireless radio of the first patch; and
providing, using first electronics on or at least partially in the first substrate and during the first time frame, a therapy to the user.

12. The method of claim 11, wherein a first component of the first electronics includes an ultrasonic transducer and the therapy includes ultrasonic therapy.

13. The method of claim 11, wherein a first component of the first electronics includes at least one conductive pad and the therapy includes electro-therapy provided through the at least one conductive pad.

14. The method of claim 11, wherein a first component of the first electronics includes at least one of a vesicle and a needle and the therapy includes a medication provided through the at least one vesicle and the at least one needle.

15. The method of claim 11, further comprising:
attaching, using a third adhesive on a third flexible and/or stretchable substrate, a third patch to skin of a user at a third location;
monitoring, using third electronics on or at least partially in the third substrate, a second biological parameter of the user during the first time frame; and
providing, using one of the first wireless radio and the second wireless radio, signals corresponding to the second biological parameter to the first wireless radio.

16. The method of claim 11, further comprising:
receiving, from the second wireless radio, signals indicating a change to the therapy provided by the first electronics, the change to the therapy determined based on the signals corresponding to the first biological parameter; and
adjusting an amount or a schedule of therapy delivery based on the signals from the second wireless radio.

17. A body area network comprising:
at least two patches, each of the at least two patches including:
a flexible and/or stretchable substrate,
an adhesive on the flexible and/or stretchable substrate, the adhesive configured to temporarily attach the patch to skin of a user, and
electronics on or at least partially in the flexible and/or stretchable substrate, the electronics including a wireless radio and at least one of a first component to provide therapy to the user and a second component to monitor a first biological parameter of the user, and
wherein electronics of a first patch of the at least two patches includes processing circuitry to receive data corresponding to the biological parameter and adjust an amount of the therapy provided by the first patch based on the received data.

18. The body area network of claim 17, wherein a second patch is configured to communicate with another device only through the wireless radio of the first patch.

19. The body area network of claim 17, wherein only one patch of the at least two patches is communicatively coupled to a device other than the at least two patches and is to communicate data from all patches of the at least two patches to the device.

20. The body area network of claim 17, wherein a first patch of the at least two patches is configured to perform a role of a master patch during a first time frame and all other patches of the at least two patches provide data to the first patch during the first time frame and a second patch of the at least two patches is configured to perform the role of the master patch during a second time frame different from the first time frame and all other patches of the at least two patches provide data to the second patch during the second time frame.

* * * * *